United States Patent
Kumar et al.

(10) Patent No.: US 6,677,485 B2
(45) Date of Patent: Jan. 13, 2004

(54) PROCESS FOR THE PREPARATION OF FLUOXETINE HYDROCHLORIDE

(75) Inventors: Naresh Kumar, Haryana (IN); Bakthavathsalan Vijayaraghavan, Haryana (IN); Kinali Venkata Ramana, Haryana (IN); Swargam Sathyanarayana, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/149,624

(22) PCT Filed: Dec. 14, 2000

(86) PCT No.: PCT/IB00/01870

§ 371 (c)(1),
(2), (4) Date: Aug. 9, 2002

(87) PCT Pub. No.: WO01/44166

PCT Pub. Date: Jun. 21, 2001

(65) Prior Publication Data

US 2003/0050508 A1 Mar. 13, 2003

(51) Int. Cl.[7] .............................................. C07C 217/02
(52) U.S. Cl. ....................................................... 564/347
(58) Field of Search .......................................... 564/347

(56) References Cited

U.S. PATENT DOCUMENTS

| | | | |
|---|---|---|---|
| 4,314,081 A | 2/1982 | Molloy, et al. | 564/347 |
| 5,166,437 A | 11/1992 | Kairisalo et al. | 564/347 |
| 5,225,585 A | 7/1993 | Schwartz et al. | 558/275 |
| 5,760,243 A | 6/1998 | Theriot | 548/240 |

FOREIGN PATENT DOCUMENTS

| | | | |
|---|---|---|---|
| GB | 2 060 618 | 5/1981 | C07C/93/14 |
| HU | 207 035 | 3/1993 | C07C/217/48 |
| WO | WO 94/00416 | 1/1994 | C07C/217/48 |

*Primary Examiner*—Samuel Barts
(74) *Attorney, Agent, or Firm*—Jayadeep R. Deshmukh Esq.; George E. Heibel, PhD.; William Hare, Esq.

(57) ABSTRACT

An improved and industrially advantageous process for the preparation of the antidepressant fluoxetine and its pharmaceutically acceptable salts, preferably hydrochloride.

6 Claims, No Drawings

PROCESS FOR THE PREPARATION OF FLUOXETINE HYDROCHLORIDE

FIELD OF THE INVENTION

The present invention relates to an improved and industrially advantageous process for the preparation of the antidepressant fluoxetine of Formula I

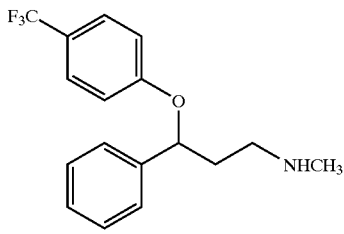

FORMULA I and its pharmaceutically acceptable salts, preferably hydrochloride.

BACKGROUND OF THE INVENTION

Chemically, fluoxetine is N-methyl-3-[(4-trifluoromethyl) phenoxy]-3-phenylpropyl amine and is a well known useful antidepressant possessing central nervous system activity. Its pharmacological effect is based on its ability to be a potent and selective brain serotonin re-uptake inhibitor without any influence on the dopamine and norepinephrine systems.

There are several methods known in the literature for the preparation of fluoxetine. One such method is known in U.S. Pat. No. 4,314,081 which claims fluoxetine per se and discloses a process which comprises reducing 3-dimethylaminopropiophenone to yield 3-dimethylamino-1-phenyl-1-propanol. This compound on treatment with thionylchloride and refuluxing the resulting chloro derivative with 4-trifluoromethyl phenol under alkaline conditions for several days to yield N, N-dimethyl-3-[4-(trifluoromethyl) phenoxy]-3-phenyl-propylamine. Selective demethylation in two steps using cyanogen bromide followed by hydrolysis with potassium hydroxide in ethylene glycol at 130° C. for about 20 hours give the desired compound fluoxetine of Formula I.

Another process for the preparation of fluoxetine is described in GB Patent No. 2,060,618 which comprises reacting sodium salt of N-methyl-3-hydroxy-3-phenylpropylamine of Formula II

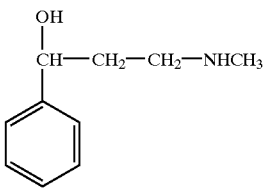

FORMULA II (formed with sodium hydride in dimethyl sulphoxide) with 1-fluoro4-(trifluoromethyl)benzene of Formula III

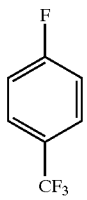

FORMULA III at high temperature.

According to Hungarian Patent No. 207,035, fluoxetine is prepared by the etherification of N-methyl-3-hydroxy-3-phenyl propylamine of Formula II with 1-chloro-4-trifluoromethyl benzene of Formula IV

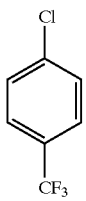

FORMULA IV in the presence of sodium amide as a base using dimethylsulphoxide as a solvent, whereas U.S. Pat. No. 5,166,437 describes the above etherification step which is carried out in solvents such as N-methyl pyrrolidone or dimethyl sulphoxide in the presence of potassium t-butoxide. U.S. Pat. No. 5,225,585 describes a process which involves use of sodium hydride in dimethylacetamide/toluene mixture in the etherification step.

The process according to PCT application WO 94/00416 also involves the etherification of N-methyl-3-hydroxy-3-phenyl propylamine of Formula II with 1-chloro-4-trifluoromethyl benzene of Formula IV in the presence of potassium hydroxide or sodium hydroxide in DMSO at a temperature between 50–120° C. for 4 to 20 hours. We carried out the etherification step in our laboratory as per the teachings of the PCT application WO 94/00416, which took about 24 hours for completion of the reaction and there was a concomitant formation of several impurities during the course of the reaction.

In our hands, we got an impure product (purity ~90%) which needed to be purified to obtain pure or pharmaceutically acceptable grade of fluoxetine hydrochloride. This ultimately resulted into significant loss of yield.

The above mentioned methods described in the prior art for the manufacture of fluoxetine of Formula I suffer several limitations, some of which are discussed below:

The methods require raw material which are highly toxic, explosive and difficult-to-handle at a commercial scale, e.g., cyanogen bromide, sodium hydride, sodium amide, thionyl chloride, potassium—t-butoxide.

The reaction conditions are unsafe which are burdened with risk of explosion and fire and hence are inconvenient to handle at a commercial scale, namely, the so-called dimsyl sodium formation in the reaction of sodium hydride with dimethyl sulphoxide. Several spontaneous decompositions, explosions and fires have been reported in connection with its preparation (Ref.: Houben-weyl, Vol. 13/1, page 304, G. Thime verlag, stuttgart (1970)].

The processes require limited available and costly raw materials such as 4-(trifluoromethyl)phenol, 1-fluoro-4-(trifluoromethyl)benzene, cyan-ogen bromide, etc.

The reactions take 20 hours to several days for completion.

The process generates a lot of effluent waste and hence is not eco-friendly.

Low overall yield and impure product.

SUMMARY OF THE INVENTION

It is an object of the present invention to solve the problems associated with the prior art and to provide an efficient method. According to one aspect of the present invention, there is provided an efficient process for the preparation of fluoxetine of Formula I and its pharmaceutically acceptable salt preferably hydrochloride which provides obvious benefits with respect to economics and convenience to operate at a commercial scale.

More particularly, the present invention relates to a process for the preparation of highly pure (purity more than 99%) fluoxetine of Formula I and its pharmaceutically acceptable acid addition salts, preferably hydrochloride, which comprises reacting N-methyl-3-hydroxy-3-phenyl propylamine of Formula II with 1-chloro-4-(trifluoromethyl)benzene of Formula IV in the presence of alkaline metal hydroxide in sulfolane in the presence of a catalyst.

The suitable alkaline metal hydroxide is selected out of sodium hydroxide and potassium hydroxide. The catalysts used in this invention are poly (ethylene glycol) -6000 and crown ethers.

The amount of solvent is at least 1 part by volume per part of N-methyl-3-hydroxy-3-phenylpropylamine of Formula II. Higher amounts of solvents and generally up to 20 parts by volume may be used. Amounts higher than 20 parts by volume are not useful from an economic point of view because large size reactors would be required.

Generally, the reaction is carried out at a temperature ranging from about 80–130° C. preferably, at 90–100° C.

The above reaction is efficiently accomplished in less than hour. However, the length of time required will vary depending upon such factors as temperature of reaction, concentration and presence or absence of efficient stirring.

After the reaction is over, the reaction mixture is cooled, a mixture of water and toluene is added. The reaction mixture is acidified with any mineral acid, preferably, hydrochloric acid. Toluene layer is separated and subjected to vacuum distillation to recover crude fluoxetine. Crude fluoxetine is crystallized from ethyl acetate to give the pure fluoxetine hydrochloride.

In the following section a preferred embodiments are described by way of examples to illustrate the process of this invention. However, this is not intended in any way to limit the scope of the present invention.

DETAILED DESCRIPTION OF THE INVENTION

EXAMPLE 1

Preparation of N-methyl-3-[(4-trifluoromethyl)phenoxy]-3-phenyl propylamine hydrochloride (fluoxetine hydrochloride)

A mixture of N-methyl-3-hydroxy-3-phenyl propylamine (MPHA, 75 gm), potassium hydroxide (150 gm) and poly (ethylene glycol)-6000 (30 gm) was charged to sulfolane (150 ml) at 90–95° C. Stirred and charged 1-chloro-4-trifluoromethylbenzene (90 gm) at 90–95° C. The reaction mixture so obtained was further stirred for about 45 minutes at 120–125° C. After the reaction was over, the reaction mixture was cooled to 20–25° C., water (990 ml) and toluene (990 ml) were added to it. Charged hydrochloric acid (300 ml) to it slowly, stirred it vigorously, and the toluene layer was separated. Toluene (900 ml) was recovered under vacuum at 60–65° C. to get crude fluoxetine hydrochloride and is crystallized from ethyl acetate to afford the pure product (134 gm, 95.7%) of purity (by HPLC) more than 99%.

EXAMPLE 2

Preparation of N-methyl-3-[(4-trifluoromethyl)phenoxy]-3-phenyl propylamine hydrochloride (fluoxetine hydrochloride)

Charged N-methyl-3-hydroxy-3-phenyl propylamine (MPHA, 15 gm) in preheated (75° C.) sulfolane (30 ml) followed by addition of potassium hydroxide (20.2 gm) and 18-crown-6 (1.0 gm). Stirred and charged 1-chloro4--trifluoromethyl benzene (22.8 gm) at 70–75° C. The reaction mixture so obtained was further stirred for about 1 hour at 95–105° C. After the reaction was over, he reaction mixture was cooled to 10° C., water (200 ml) and toluene (200 ml) were added to it. Charged hydrochloric acid (33 ml) at 10–15° C., stirred and toluene layer was separated. Recovered toluene (-190 ml) under vacuum at 60–65° C. to get crude fluoxetine hydrochloride and is crystallized from toluene to afford the pure product (27.5 gm, 98.4%) of purity –99% (by HPLC).

While the present invention has been described in terms of its specific embodiments, certain modifications and equivalents will be apparent to those skilled in the art and are intended to be included within the scope of the present invention.

We claim:

1. A process for the preparation of pure fluoxetine of the following formula:

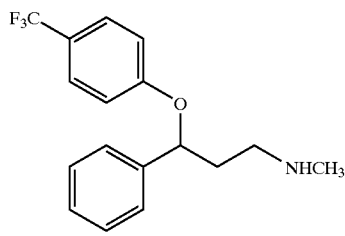

and its pharmaceutically acceptable acid addition salts which comprises reacting N-methyl-3-hydroxy-3-phenyl propylamine of the following formula:

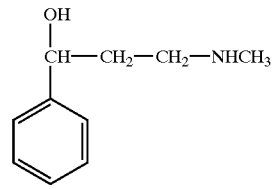

with 1-chloro4-(trifluoromethyl) benzene of the following formula:

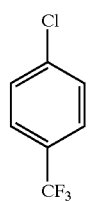

in the presence of alkaline metal hydroxide in sulfolane in the presence of a catalyst.

2. A process of claim 1, which comprises using sodium or potassium hydroxide as an alkaline metal hydroxide.

3. A process of claim 1 wherein the reaction temperature is in the range 80–130° C.

4. A process of claim 3 wherein the reaction temperature is in the range of 90–95° C.

5. A process of claim 1 wherein the reaction is carried out in presence of a catalytic amount of Poly (ethylene glycol 6000 or crown ethers.

6. A process of claim 5 wherein the reaction is carried out in presence of catalytic amount of Poly (ethylene) glycol 6000.

* * * * *

UNITED STATES PATENT AND TRADEMARK OFFICE
CERTIFICATE OF CORRECTION

PATENT NO. : 6,677,485 B2
DATED : January 13, 2004
INVENTOR(S) : Kumar et al.

It is certified that error appears in the above-identified patent and that said Letters Patent is hereby corrected as shown below:

Column 1,
Line 67, "fluoro4" should be -- fluoro-4 --
Line 20, "chloro4" should be -- chloro-4- --
Line 23, "he" should be -- the --
Line 28, "-190" should be -- ~190 --
Line 31, "-99%" should be -- ~99% --.
Line 66, "chloro4" should be -- chloro-4 --

Column 6,
Lines 6-7, "glycol 6000" should be -- glycol)-6000 --

Signed and Sealed this

Twenty-seventh Day of July, 2004

JON W. DUDAS
*Acting Director of the United States Patent and Trademark Office*